(12) United States Patent
Maloney et al.

(10) Patent No.: US 10,624,751 B2
(45) Date of Patent: *Apr. 21, 2020

(54) KNEE IMPLANT SYSTEM

(71) Applicant: MicroPort Orthopedic Holdings Inc., Tiel (NL)

(72) Inventors: William J. Maloney, Palo Alto, CA (US); J. David Blaha, Ann Arbor, MI (US); C. Lowry Barnes, Little Rock, AR (US); John M. Green, Arlington, TN (US); David R. Tuttle, Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/161,039

(22) Filed: Oct. 15, 2018

(65) Prior Publication Data
US 2019/0046325 A1    Feb. 14, 2019

Related U.S. Application Data

(63) Continuation of application No. 15/811,537, filed on Nov. 13, 2017, now Pat. No. 10,098,748, which is a continuation of application No. 15/200,465, filed on Jul. 1, 2016, now Pat. No. 9,814,586, which is a continuation of application No. 13/840,931, filed on Mar. 15, 2013, now Pat. No. 9,381,088, which is a continuation of application No. 13/009,158, filed on Jan. 19, 2011, now Pat. No. 8,403,994.

(51) Int. Cl.
*A61F 2/38* (2006.01)
*A61F 2/30* (2006.01)

(52) U.S. Cl.
CPC ............ *A61F 2/3859* (2013.01); *A61F 2/389* (2013.01); *A61F 2002/30616* (2013.01); *A61F 2002/30892* (2013.01)

(58) Field of Classification Search
CPC ........... A61F 2/3859; A61F 2/389; A61F 2/38
See application file for complete search history.

(56) References Cited

U.S. PATENT DOCUMENTS 8,790,411 B2 * 7/2014 Mandell .................. A61F 2/389
623/20.35

* cited by examiner

Primary Examiner — Jason-Dennis N Stewart

(57) ABSTRACT

Knee prosthesis includes a femoral component adapted to fit on a distal end of the femur and a tibial insert component. The femoral component includes a measured anterior/posterior dimension defined by the posterior condyle surface and the interior surface of the anterior flange and a distal peg provided on a distal bone facing surface of each of the lateral and medial condylar structures, wherein the distal pegs are positioned at a midpoint of the measured anterior/posterior dimension. The implant system provides two distinct sizing segments and the tibial insert has a medial tibial aspect ratio of 0.74 and a lateral tibial aspect ratio of 0.65 to 0.68 for all sizes.

19 Claims, 8 Drawing Sheets

KNEE IMPLANT SYSTEM

CROSS-REFERENCE TO RELATED APPLICATIONS

This patent application is a continuation of U.S. patent application Ser. No. 15/811,537, filed Nov. 13, 2017, now U.S. Pat. No. 10,098,748, which is a continuation of U.S. patent application Ser. No. 15/200,465, filed Jul. 1, 2016, now U.S. Pat. No. 9,814,586, which is a continuation of U.S. patent application Ser. No. 13/840,931, filed Mar. 15, 2013, now U.S. Pat. No. 9,381,088, which is a continuation of U.S. patent application Ser. No. 13/009,158, filed Jan. 19, 2011, now U.S. Pat. No. 8,403,944. The disclosures of the foregoing applications are incorporated herein by reference.

FIELD OF THE INVENTION

The present disclosure relates generally to knee prostheses that more closely emulate the kinematics of the actual knee joint.

BACKGROUND

Modern total knee arthroplasty implants replace three separate articulating surfaces within the knee joint: the patello-femoral compartment and the lateral and medial inferior tibio-femoral compartments. Most currently available implants for Total Knee Replacement (TKR) are designed to articulate from a position of slight hyperextension to approximately 115° to 130° flexion. A tricompartmental design can meet the needs of most TKR patients even though the healthy human knee is capable of a range of motion (ROM) approaching 170°. However, there are some TKR patients who have a particular need to obtain high flexion in the knee joint. For many, a TKR that permits patients to achieve a ROM in excess of 130° is desirable to allow deep kneeling, squatting and sitting on the floor with the legs tucked underneath.

Conventional TKR implants do not produce normal knee kinematics or motion and generally have a limited range of motion as compared to that of a normal knee. This is because conventional TKR implants flex by rotating about a generally horizontal axis during flexion and extension, whereas the kinematics of a natural knee joint involves more complex motion of the femur and tibia relative to one another. For example, in a natural knee, the tibia rotates internally about the longitudinal axis of the tibia during flexion.

Although some attempts have been made to design a total knee prosthesis which replicates the kinematics of a natural knee, there exists a room for more improvement.

SUMMARY

According to an embodiment of the present disclosure, a knee prosthesis for replacement of at least a portion of a knee joint in a leg of a patient is disclosed. The knee prosthesis comprises a femoral component adapted to fit on a distal end of the femur and a tibial insert component adapted to fit on a tibial base component. The femoral component comprises a lateral condylar structure and a medial condylar structure, the lateral condylar structure defining a lateral condylar surface and the medial condylar structure defining a medial condylar surface. The femoral component also includes a measured anterior/posterior dimension defined by the posterior condyle surface and the interior surface of the anterior flange. A distal peg is provided on a distal bone facing surface of each of the lateral and medial condylar structures, wherein the distal pegs are positioned at a midpoint of the measured anterior/posterior dimension.

The medial condylar structure of the femoral component can be described as a spherical surface, extending from the posterior portion of the medial condyle to the anterior portion of the medial condyle. The lateral condylar structure of the femoral component can be described as ovoid, with the posterior portion of the lateral condyle being spherical, but the anterior portion of the lateral condyle having different sets of radii in the sagittal (side) and coronal (front) planes.

The tibial insert comprises a lateral bearing surface, a medial bearing surface, a medial anterior/posterior dimension, a lateral anterior/posterior dimension, and a medial/lateral dimension, wherein the ratio of the medial anterior/posterior dimension to the medial/lateral dimension is 0.74 and the ratio of the lateral anterior/posterior dimension to the medial/lateral dimension is 0.66 to 0.68. The lateral condylar surface of the tibial insert is configured to contact the lateral bearing surface and the medial condylar surface is configured to contact the medial bearing surface when the knee prosthesis is installed in the leg of a patient.

The knee prosthesis of the present disclosure provides a primary total knee arthroplasty implant that is stable in the primary areas of gait while permitting the patient to achieve deep flexion (flexion angles greater than 120°). The knee prosthesis is stable throughout its functional flexion by providing features that resist paradoxical motion and promote deep flexion.

BRIEF DESCRIPTION OF THE DRAWINGS

The features shown in the above referenced drawings are illustrated schematically and are not intended to be drawn to scale nor are they intended to be shown in precise positional relationship. Like reference numbers indicate like elements.

DETAILED DESCRIPTION

Figure 1:
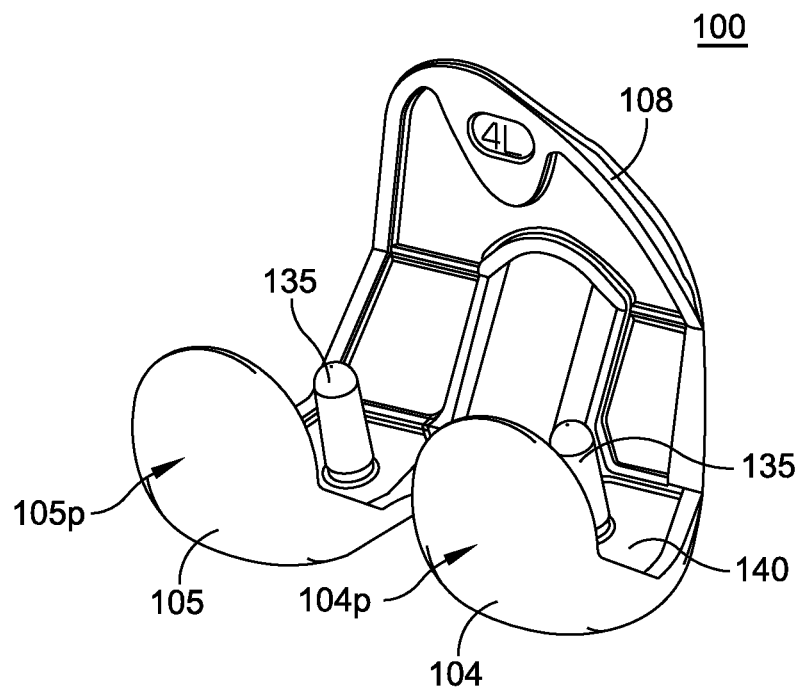
FIG. 1 is a perspective view of an embodiment of a left knee femoral component of a knee prosthesis system of the present disclosure.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Figures 6, 7:
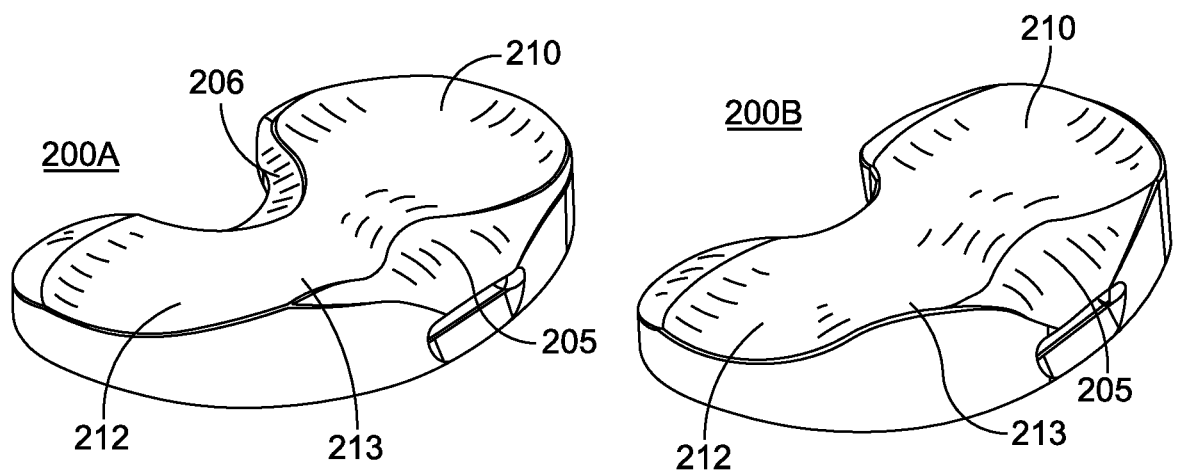
FIG. 6 is a perspective view of an embodiment of a left knee tibial insert component of a knee prosthesis system of the present disclosure.
FIG. 7 is a perspective view of another embodiment of a left knee tibial insert component of a knee prosthesis system of the present disclosure.
Figure 2:
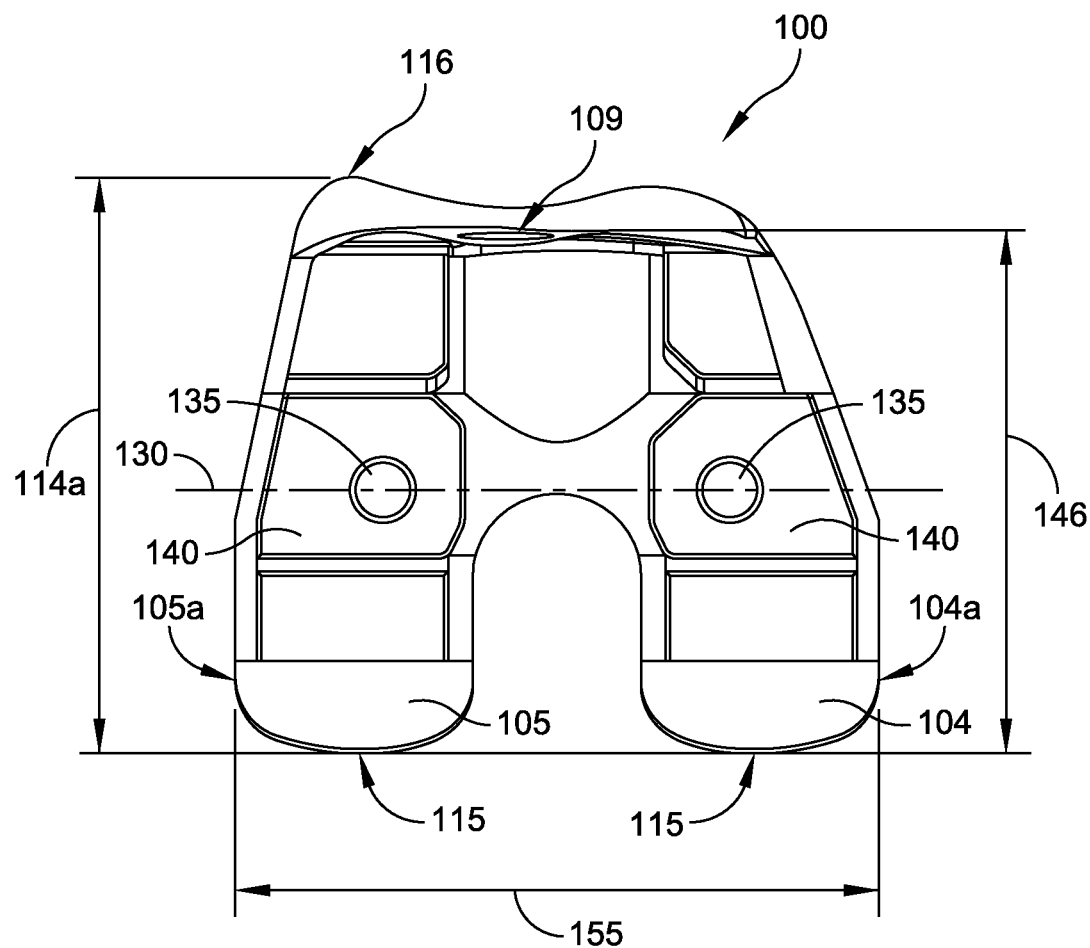
FIG. 2 is a top down view of the femoral component of FIG. 1.
Figure 3:
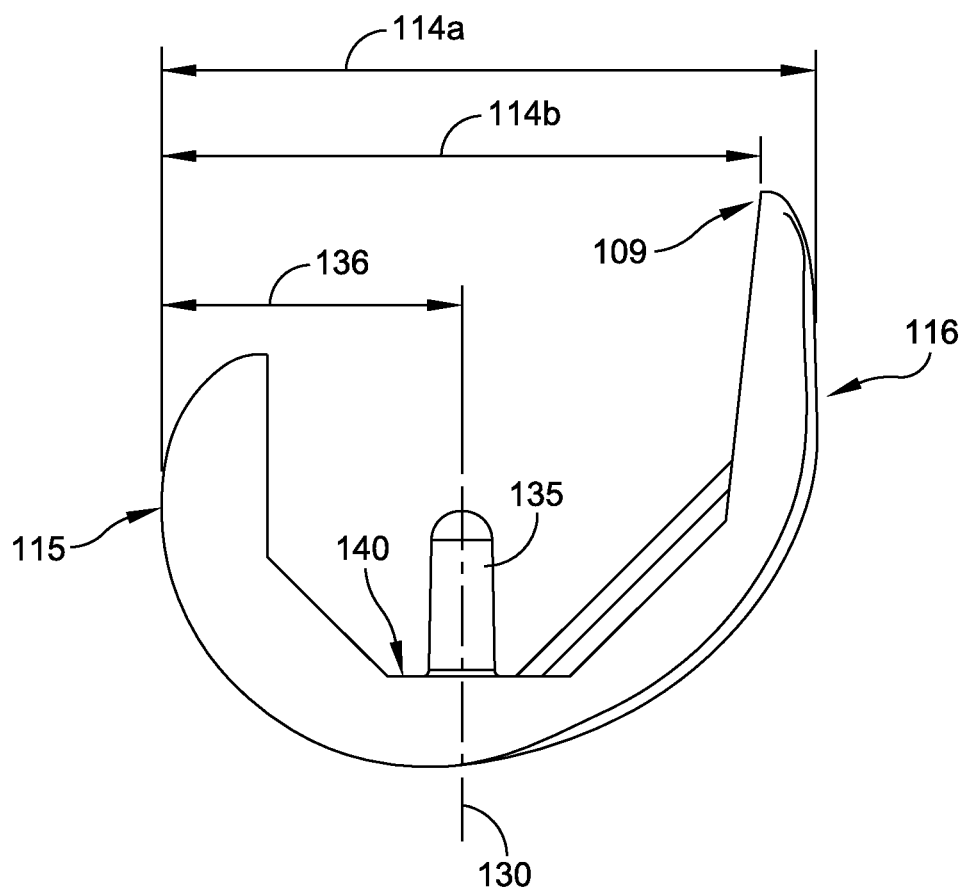
FIG. 3 is a side view of the femoral component of FIG. 1.

FIGS. 1-3 show a femoral component 100 of a knee prosthesis of the present disclosure. FIG. 6 shows one embodiment of a tibial insert component 200A of the knee prosthesis. FIG. 7 shows another embodiment of a tibial insert component 200B of the knee prosthesis.

Referring to FIG. 1, the femoral component 100 has a medial condyle 104 and a lateral condyle 105 providing medial and lateral condylar surfaces that cooperate with the corresponding bearing surfaces on the tibial inserts 200A or 200B (shown in FIGS. 6 and 7, respectively). Referring to FIGS. 2 and 3, the femoral component 100 includes a femoral anterior/posterior dimension 114a that extends from the posterior condylar surface 115 of the lateral condyle 105 to the lateral anterior condyle surface 116. The femoral component 100 also includes a femoral measured anterior/posterior dimension 114b that extends from the posterior condyle surfaces 115 to the proximal tip 109 of the interior surface of the anterior flange 108, which references the anterior cortex of the distal portion of the femur of the patient anatomy.

The femoral component 100 has at least two distal pegs 135, one distal peg on the bone facing surface 140 of each of the lateral and medial condylar structures, that are used for medial/lateral stability for the femoral component 100 when installed on a patient's femur. The femoral component 100 is offered in a variety of sizes with progressively increasing the femoral measured anterior/posterior dimensions 114b that will accommodate the varying dimensions seen in the same measure of the patient anatomy. The distal pegs 135 are also used for instrumenting the position of the femoral component on the femur.

However, unlike the femoral components in conventional knee prosthesis systems, in which the various sizes of the femoral components are referenced either from the anterior cortex surface of the distal portion of the femur or the posterior condyles of the distal portion of the femur, the various sizes of the femoral component 100 of the knee prosthesis of the present disclosure are referenced from the midline 130 of the measured anterior/posterior dimension 114b of the femoral implant component 100. The distal pegs 135, provided on the bone facing surface 140 of each of the medial and lateral condyles 104, 105 are located along the midline 130 of the femoral component 100. The measure for size for any knee implant system is the measure from the tangent from the posterior condyles to the anterior cortex; this is similar to the femoral measured anterior/posterior dimension 114b. In the knee implant system of the present disclosure, the distal pegs 135 are positioned at the midpoint of the femoral measured anterior/posterior dimension 114b.

Figure 4:
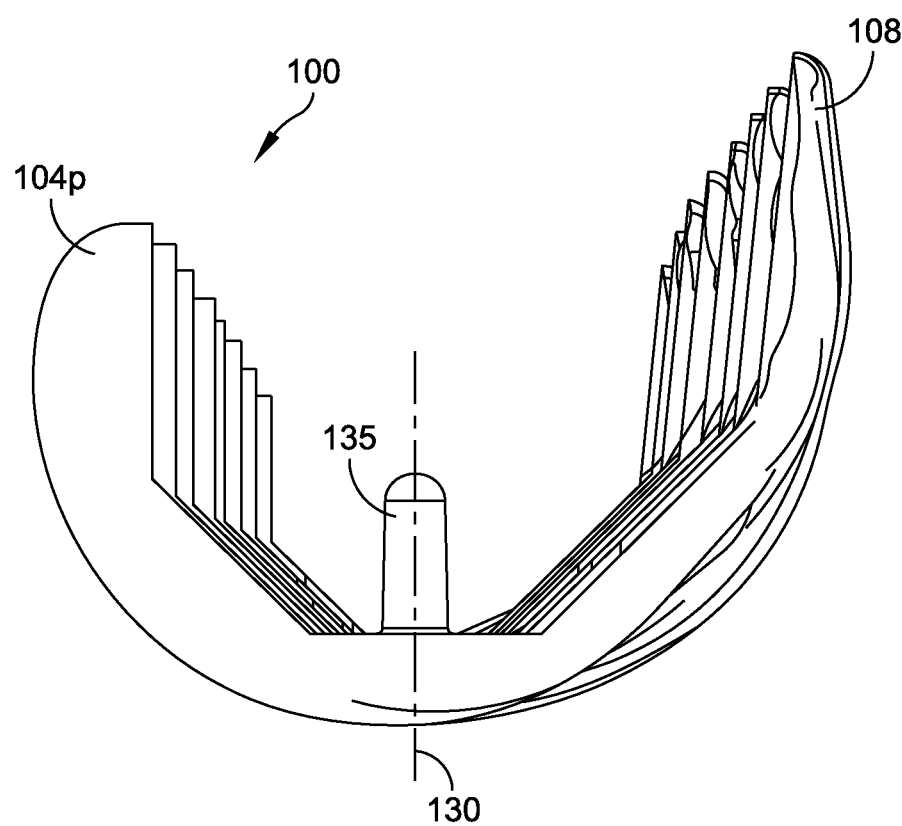
FIG. 4 is a side view composite illustration of several sizes of the femoral component shown in FIG. 1.

Thus, the distance from the posterior condyle surface 115 to the midline 130 is one-half of the femoral measured anterior/posterior dimension 114b. Therefore, all sizes of the femoral component 100 are referenced from the midline 130 represented by the position of the distal pegs 135. This is illustrated in FIG. 4 which is a side-view composite illustration of several sizes of the femoral component 100.

As the femoral component 100 reduces in size, both the anterior flange 108 and the posterior portions 104p and 105p of the condyles get closer toward the distal pegs 135. This sizing method requires bone resections on both the anterior side and posterior side of the distal end of the patient's femur thus ensuring that new bone surfaces are provided for interfacing with the femoral component 100 when the surgeon downsizes the femoral component 100 during fitting process.

This is particularly important for cement free implants that require interface of cut bone with the bone ingrowth surfaces of the implant and that gaps are not present at the implant/bone interface. This method of growth from size to size of the present disclosure reduces the amount of bone removed from either anterior or posterior compartment by half when a smaller size is chosen from this "mid-line" frame of reference.

Conventional knee systems that "grow" their implant from either the anterior side or posterior side only will require that all the bone is removed from the side opposite from the reference surface when downsizing of the implant is required. This can be problematic in the conventional referencing systems. An anterior referencing system will have a tendency to remove posterior condylar bone when downsizing, opening the flexion gap and reducing posterior condylar offset (dimension from tangent of the posterior condyles of the femoral implant to the posterior cortex of the distal femoral bone) which can create instability and reduce flexion respectively. Conversely, a posterior referencing system will have a tendency to either overstuff the patella-femoral gap if the component is too large or risk notching (resulting in an undercut) the anterior cortex of the distal femoral bone which may reduce flexion or increase the risk of femoral bone fracture respectively.

Each size femoral component 100 has the femoral anterior/posterior dimension 114a, the femoral measured anterior/posterior dimension 114b, and a femoral medial/lateral dimension 155. The ratio of one measure, the femoral anterior/posterior dimension 114a to the femoral medial/lateral dimension 155, is defined as femoral aspect ratio, which is a measure of distal femoral profile. The ratio of another measure, the femoral measured anterior/posterior dimension 114b to the femoral medial/lateral dimension 155, referred to as the measured aspect ratio, is a measure more pertinent to implants as this is the datum reference between the posterior condyles and the proximal tip 109 of the interior surface of the anterior flange 108, the surface that contacts the anterior cortex of the distal portion of the femur of the patient anatomy.

The knee prosthesis system of the present disclosure comprises two distinct sizing segments with different femoral aspect ratio ranges. A wider primary size range has a femoral aspect ratio of 0.87 to 0.95 and a narrower stature size range has a femoral aspect ratio range of 0.97 to 1.00. The measured aspect ratio, the ratio of the femoral measured anterior/posterior dimension 114b to the femoral medial/lateral dimension 155, is also defined by two sizing segments; a wider primary size range has a femoral aspect ratio range of 0.80 to 0.87 and a narrower stature size range has a femoral aspect ratio range of 0.89 to 0.91. This provides significant benefit over the conventional knee systems where only one size segment is offered for a given measured anterior/posterior dimension.

The availability of offering two distinct sizing segments for a given measured anterior/posterior dimension 114b provides the benefit of optimizing the fit of the implant for a multitude of patient populations. Conventional knee systems that offer only one size segment for a given measured anterior/posterior dimension may not accommodate all of the variations seen for a given patient populations and as a result may deviate from a desired size for a given patient and create potential complications as a result (i.e. reduced posterior condylar offset, notching the anterior cortex, etc.). The options offered in the present disclosure provide an attempt to reduce these complications from occurring by providing the optimal size prosthesis.

Figure 5:
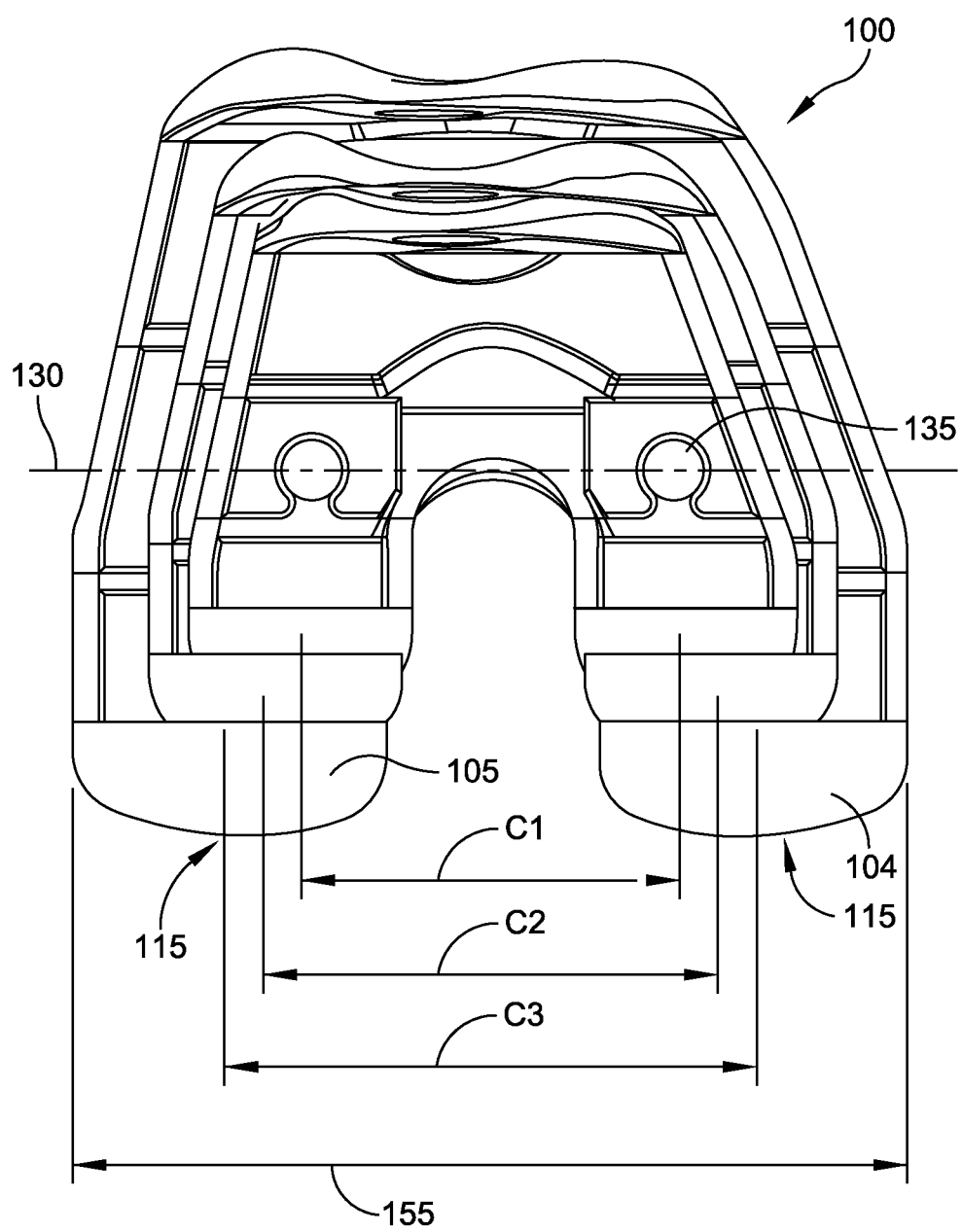
FIG. 5 is top down view composite illustration of several sizes of the femoral component shown in FIG. 1.
Figure 8:
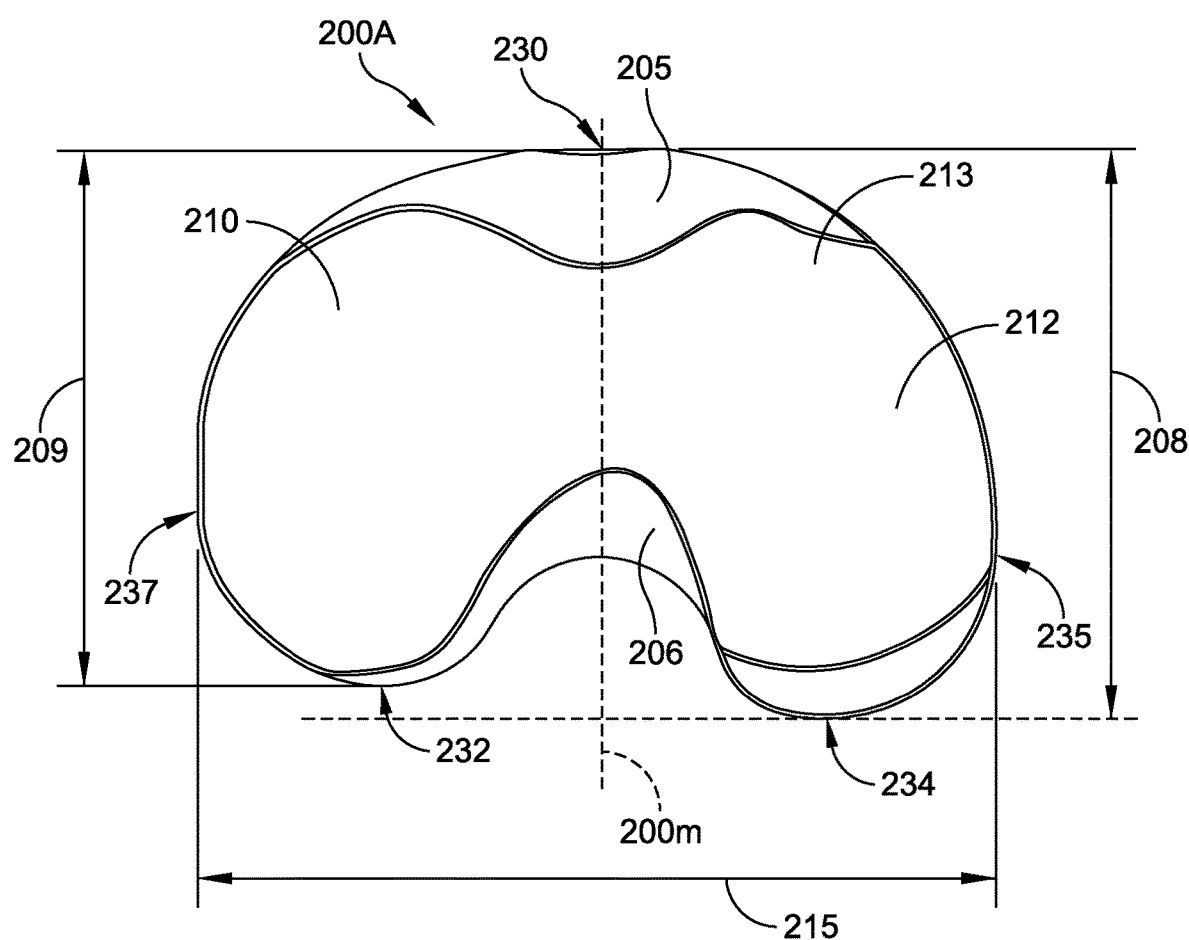
FIGS. 8-10 are top down views of the left knee tibial insert component of FIG. 6.
Figure 9:
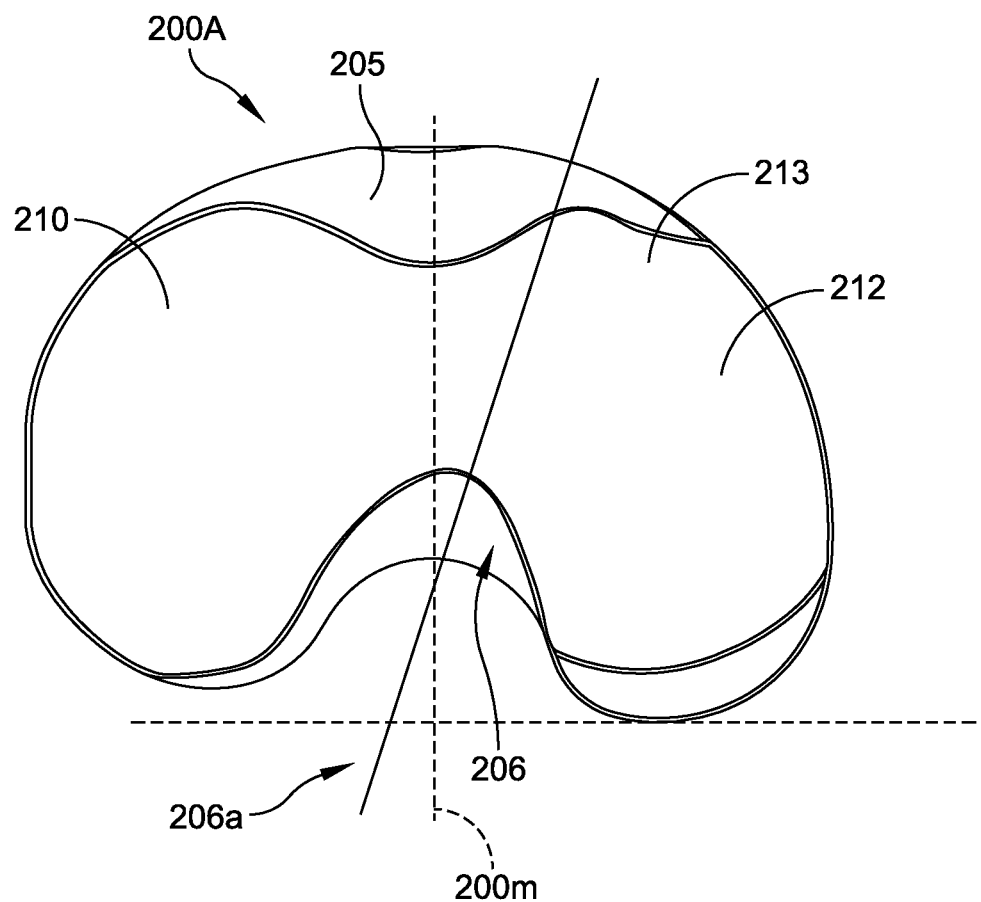
Figure 10:
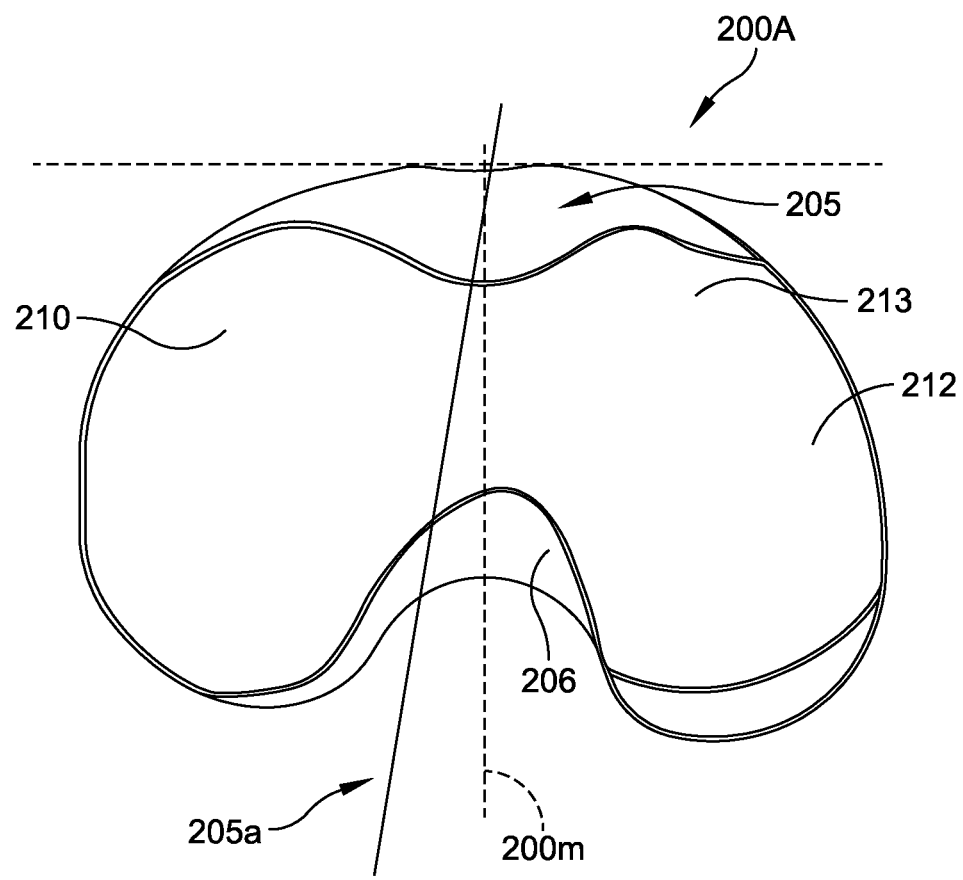

Referring to FIG. 5, which is a composite illustration of several sizes of the femoral component 100, each distal femoral implant 100 size also has their own femoral medial/lateral dimension 155 and furthermore their own condylar spacing dimension contained within three groups: C1, C2 and C3. Condylar spacing dimension is the distance between the articulating high points from medial condyle 104 and lateral condyle 105. The knee prosthesis system of the present disclosure comprises three distinct condylar spacing ratio ranges, defined by the dimension between medial and lateral condyle apex over the implant medial/lateral dimension 155 of the femoral prosthesis 100. The group C1 has a condylar spacing ratios in the range of 0.59 to 0.62. The wider sizing segment of group C2 has a condylar spacing ratios in the range of 0.55 to 0.64. The narrower sizing segment of group C2 has a condylar spacing ratios in the range of 0.60 to 0.69. The group C3 has a condylar spacing ratios in the range of 0.60 to 0.63.

Referring to FIGS. 6-10, the tibial inserts 200A and 200B are configured with a tissue friendly notch 205 for the patella tendon located at the anterior side of the tibial inserts 200A and 200B. The medial/lateral midline 200m notes the neutral position of the component. The notch 205 is angled in the direction 205a of the quadriceps pull. The notch 205 helps prevent or relieve potential impingement of the patella tendon during knee flexion. The tibial inserts 200A and 200B are also configured with an anterior lip 213 on anterior portion of the medial compartment 212. This anterior lip 213 provides the structure to prevent translation of the femoral component 100 during early gait.

The tibial insert embodiment 200A, which is intended to be implanted with the posterior cruciate ligament (PCL) in place and is provided with a tissue friendly notch 206 for the PCL that is angled in the direction 206a of the PCL pull. The tibial insert embodiment 200B is intended to be implanted where the PCL has been removed and thus the tissue friendly notch 206 is not necessary.

Each size tibial insert implants 200A, 200B has a tibial medial anterior/posterior dimension 208, a tibial lateral anterior/posterior dimension 209, and a tibial medial/lateral dimension 215. The knee implant system of the present disclosure is characterized by particular ratios of these dimensions. The ratio of the tibial medial anterior/posterior dimension 208 to the tibial medial/lateral dimension 215 is referred to as the medial tibial aspect ratio and the ratio of the tibial lateral anterior/posterior dimension 209 to the tibial medial/lateral dimension 215 are defined as the lateral tibial aspect ratio. These dimensional ranges provide the knee implant system of the present disclosure to optimally fit the patient population. The knee implant system of the present disclosure has a medial tibial aspect ratio of about 0.74 for all sizes and a lateral tibial aspect ratio in the rage of about 0.65 to 0.68. Additionally, the % difference between the medial anterior/posterior dimension 208 and the lateral anterior/posterior dimension 209 ranges from 9.6% to 13.3%. The % difference is calculated by ((medial anterior/posterior dimension 208)−(lateral anterior/posterior dimension 209)/lateral anterior/posterior dimension 209). Conventional knee systems either provide a symmetric implant that will leave portions of the proximal tibial resection uncovered, or are not symmetric enough where patient anatomy trends to become more asymmetric as the knee becomes larger. The knee implant system of the present disclosure trends to have a more asymmetric tibial prosthesis for larger tibial implants.

The knee implant system comprising the distal femoral component 100, the tibial insert components 200A and 200B, and the tibial base component that the tibial insert components interface with, provides the surgeon with implants of varying sizing options to enable more accurate fitting to a given patient's anatomic requirements. The knee implant system of the present disclosure also provides more natural knee joint kinematics promoted by the structures described above. For example, the anterior lip 213 of the tibial insert components 200A, 200B prevent or limit the anterior translation of the femoral component 100 during flexion and permitting a spinning motion of the medial condyle 104 on the medial compartment 212 of the tibial insert component 200A and 200B, while permitting a rolling motion of the lateral condyle 105 on the lateral compartment 210 of the tibial insert component 200A and 200B.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention. The scope of the invention disclosed herein is to be limited only by the following claims.

What is claimed is:

1. A knee implant system for reducing an amount of bone removed from an anterior and a posterior side of a femur comprising:
   a plurality of femoral components of various sizes, wherein each of the various sizes of the femoral components is referenced from a midline of a measured anterior/posterior dimension of the femoral implant component, the measured anterior/posterior dimension defined by posterior condyle surfaces and a proximal tip of an interior surface of an anterior flange, such that as the femoral components reduce in size, the proximal tip of the anterior flange and the posterior condyle surfaces get closer toward the midline, and
   each of said femoral components having a medial condyle having a medial condylar surface, the medial condylar surface being a spherical surface extending from a posterior portion of the medial condyle to an anterior portion of the medial condyle.

2. The knee implant system of claim 1, wherein for each reduction in femoral component size, the proximal tip of the anterior flange and the posterior condyles get closer toward the midline at an equal rate.

3. The knee implant system of claim 1, further comprising each of the femoral components having a distal peg on a bone facing surface of each of a lateral and the medial condyle, wherein the distal pegs are positioned on the midline.

4. The knee implant system of claim 3, wherein the plurality of femoral components comprises two distinct sizing segments with different femoral aspect ratio ranges, the femoral aspect ratio defined as the ratio of the femoral anterior/posterior dimension to the femoral medial/lateral dimension, wherein the femoral anterior/posterior dimension extends from the posterior condylar surface of a lateral condyle to a lateral condylar surface, wherein the two distinct sizing segments with different femoral aspect ratio ranges comprise:
- a wider primary size range having a femoral aspect ratio of 0.87 to 0.95, and
- a narrower stature size range having a femoral aspect ratio range of 0.97 to 1.00.

5. The knee implant system of claim 3, wherein the plurality of femoral components comprises two distinct sizing segments with different measured aspect ratio ranges, the measured aspect ratio defined as the ratio of the femoral measured anterior/posterior dimension to the femoral medial/lateral dimension, wherein the two distinct sizing segments with different measured aspect ranges comprise:
- a wider primary size range having a femoral aspect ratio range of 0.80 to 0.87 and
- a narrower stature size range having a femoral aspect ratio range of 0.89 to 0.91.

6. The knee implant system of claim 3, wherein the femoral components have a femoral aspect ratio of 0.87 to 0.95 and a measured aspect ratio of 0.80 to 0.87,
wherein the femoral aspect ratio is the ratio of the femoral anterior/posterior dimension to the femoral medial/lateral dimension and the measured aspect ratio is the ratio of the femoral measured anterior/posterior dimension to the femoral medial/lateral dimension, wherein
- the femoral anterior/posterior dimension extends from the posterior condylar surface of the lateral condyle to the lateral condylar surface, and
- the femoral medial/lateral dimension extends from the lateral side of the lateral condyle to the medial side of the medial condyle.

7. The distal femoral component of claim 6, wherein the femoral components have a condylar spacing ratio of 0.59 to 0.62, wherein the condylar spacing ratio is the ratio of the dimension between medial and lateral posterior condylar apex to the femoral medial/lateral dimension.

8. The distal femoral component of claim 6, wherein the femoral components have a condylar spacing ratio of 0.55 to 0.64, wherein the condylar spacing ratio is the ratio of the dimension between medial and lateral posterior condylar apex to the femoral medial/lateral dimension.

9. The distal femoral component of claim 6, wherein the femoral components have a condylar spacing ratio of 0.60 to 0.63, wherein the condylar spacing ratio is the ratio of the dimension between medial and lateral posterior condylar apex to the femoral medial/lateral dimension.

10. The distal femoral component of claim 6, wherein the femoral components have a condylar spacing ratio of 0.60 to 0.69, wherein the condylar spacing ratio is the ratio of the dimension between medial and lateral posterior condylar apex to the femoral medial/lateral dimension.

11. The distal femoral component of claim 3, wherein the femoral components have a femoral aspect ratio of 0.97 to 1.00 and a measured aspect ratio of 0.89 to 0.91,
wherein the femoral aspect ratio is the ratio of the femoral anterior/posterior dimension to the femoral medial/lateral dimension and the measured aspect ratio is the ratio of the femoral measured anterior/posterior dimension to the femoral medial/lateral dimension, wherein
- the femoral anterior/posterior dimension extends from the posterior condylar surface of the lateral condyle to the lateral condylar surface, and
- the femoral medial/lateral dimension extends from the lateral side of the lateral condyle to the medial side of the medial condyle.

12. The knee implant system of claim 1, wherein the plurality of femoral components comprises two distinct sizing segments with different femoral aspect ratio ranges, the femoral aspect ratio defined as the ratio of the femoral anterior/posterior dimension to the femoral medial/lateral dimension, wherein the femoral anterior/posterior dimension extends from the posterior condylar surface of a lateral condyle to a lateral condylar surface, wherein the two distinct sizing segments with different femoral aspect ratio ranges comprise:
- a wider primary size range having a femoral aspect ratio of 0.87 to 0.95, and
- a narrower stature size range having a femoral aspect ratio range of 0.97 to 1.00.

13. The knee implant system of claim 1, wherein the plurality of femoral components comprises two distinct sizing segments with different measured aspect ratio ranges, the measured aspect ratio defined as the ratio of the femoral measured anterior/posterior dimension to the femoral medial/lateral dimension, wherein the two distinct sizing segments with different measured aspect ranges comprise:
- a wider primary size range having a femoral aspect ratio range of 0.80 to 0.87 and
- a narrower stature size range having a femoral aspect ratio range of 0.89 to 0.91.

14. The knee implant system of claim 1, wherein the femoral components have a femoral aspect ratio of 0.87 to 0.95 and a measured aspect ratio of 0.80 to 0.87,
wherein the femoral aspect ratio is the ratio of the femoral anterior/posterior dimension to the femoral medial/lateral dimension and the measured aspect ratio is the ratio of the femoral measured anterior/posterior dimension to the femoral medial/lateral dimension, wherein
- the femoral anterior/posterior dimension extends from the posterior condylar surface of the lateral condyle to the lateral condylar surface, and
- the femoral medial/lateral dimension extends from the lateral side of the lateral condyle to the medial side of the medial condyle.

15. The distal femoral component of claim 14, wherein the femoral components have a condylar spacing ratio of 0.59 to 0.62, wherein the condylar spacing ratio is the ratio of the dimension between medial and lateral posterior condylar apex to the femoral medial/lateral dimension.

16. The distal femoral component of claim 14, wherein the femoral components have a condylar spacing ratio of 0.55 to 0.64, wherein the condylar spacing ratio is the ratio of the dimension between medial and lateral posterior condylar apex to the femoral medial/lateral dimension.

17. The distal femoral component of claim 14, wherein the femoral components have a condylar spacing ratio of 0.60 to 0.63, wherein the condylar spacing ratio is the ratio of the dimension between medial and lateral posterior condylar apex to the femoral medial/lateral dimension.

18. The distal femoral component of claim 14, wherein the femoral components have a condylar spacing ratio of 0.60 to 0.69, wherein the condylar spacing ratio is the ratio of the dimension between medial and lateral posterior condylar apex to the femoral medial/lateral dimension.

19. The distal femoral component of claim 1, wherein the femoral components have a femoral aspect ratio of 0.97 to 1.00 and a measured aspect ratio of 0.89 to 0.91,
wherein the femoral aspect ratio is the ratio of the femoral anterior/posterior dimension to the femoral medial/lateral dimension and the measured aspect ratio is the ratio of the femoral measured anterior/posterior dimension to the femoral medial/lateral dimension, wherein the femoral anterior/posterior dimension extends from the posterior condylar surface of the lateral condyle to the lateral condylar surface, and
the femoral medial/lateral dimension extends from the lateral side of the lateral condyle to the medial side of the medial condyle.

\* \* \* \* \*